United States Patent [19] [11] 4,325,971
Poyser et al. [45] Apr. 20, 1982

[54] METOCLOPRAMIDE/PARACETAMOL TABLETS

[75] Inventors: Robert H. Poyser, Old Harlow; David H. Turner, London, both of England

[73] Assignee: Beecham Group Limited, England

[21] Appl. No.: 94,503

[22] Filed: Nov. 15, 1979

[30] Foreign Application Priority Data

Nov. 16, 1978 [GB] United Kingdom ............... 44842/78

[51] Int. Cl.³ .................. A61K 31/165; A61K 31/615
[52] U.S. Cl. ..................................... 424/324; 424/233
[58] Field of Search ................................ 424/233, 324

[56] References Cited

U.S. PATENT DOCUMENTS 3,424,842  1/1969  Nurnberg ............................... 424/94
4,097,606  1/1978  Chavkin et al. ...................... 424/324

FOREIGN PATENT DOCUMENTS 2247206  5/1975  France .
1442159  7/1976  United Kingdom .

OTHER PUBLICATIONS

*Drugs*, 12, 1976, pp. 81–131, Adis Press.
Br. J. Clin. Pharmac. (1978), 5, 337–339.
Chem. Abst. 83-37899q, (1975).
Chem. Abst. 78-58100J (1973).
Merck Index, 9th Ed. (1976), p. 36 & 873.

*Primary Examiner*—Stanley J. Friedman
*Attorney, Agent, or Firm*—Jacobs & Jacobs

[57] ABSTRACT

Analgesic tablets which comprise an analgesic Medicament and metoclopramide or an acid addition salt thereof, the weight ratio of analgesic to metoclopramide or acid addition salt thereof lying in the range of 50:1 to 250:1, and a process for their preparation.

5 Claims, No Drawings

METOCLOPRAMIDE/PARACETAMOL TABLETS

This invention relates to tablets comprising a combination of an analgesic medicament and metoclopramide or an acid addition salt thereof, and to a process for their preparation.

It is known that metoclopramide, parenterally administered, potentiates the effect of an orally administered analgesic.

Surprisingly, we have now found that the oral administration of a novel type of coformulation of an analgesic with a non-analgesic active ingredient, i.e. metoclopramide, is beneficial in the treatment of migraine headache.

Accordingly, the present invention provides an analgesic tablet, which tablet comprises an analgesic medicament and metoclopramide or an acid addition salt thereof, the weight ratio of analgesic to metoclopramide or acid addition salt thereof lying in the range of 50:1 to 250:1.

The analgesic medicament may be selected from known analgesics such as paracetamol, acetylsalicylic acid or conventional analgesic derivatives thereof, and the like, However, any analgesic medicament which does not give rise to undesirable reactions with the other materials of the tablet may be employed. Suitable medicaments will be known to the skilled man or will be readily and routinely ascertainable by such. The analgesic is preferably paracetamol or acetylsalicylic acid. Paracetamol D.C. is particularly preferred, that is paracetamol coated with hydrolysed gelatin. (This form of paracetamol is well known in the formulation art and commercially available).

The acid addition salt of metoclopramide is suitably any pharmaceutically acceptable salt such as the hydrochloride.

The metoclopramide or its acid addition salt is suitably present as 0.1 to 2.5 percent by weight of the tablet, preferably as 0.25 to 2.0 percent by weight.

The weight ratio of analgesic to metoclopramide suitably lies in the range of 60:1 to 140:1, preferably in the range of 80:1 to 120:1.

The tablet may contain a conventional unit dose of each medicament although multiples and sub-multiples of such unit doses may be incorporated as convenient.

It will be appreciated that it will often be convenient to incorporate half a unit dose of each medicament in each tablet.

Suitable unit doses of the analgesic lie in the range of 0.6 to 1.4 g., more generally 0.8 to 1.2 g.

Suitable unit doses of metoclopramide or an acid addition salt thereof lie in the range 5 to 15 mg, more generally 8 to 12 mg.

The tablet may contain other components conventionally used in the art of tablet formulation such as lubricants, for example magnesium stearate and stearic acid; disintegrants, for example cellulose derivatives, starches, binders, for example modified starches and cellulose derivatives; glidants, for example colloidal silicas; compression aids, for example cellulose derivatives; and colourants.

A preferred disintegrant and compression aid in the tablets of the present invention is Avicel (Registered Trade Mark).

As will be apparent from the foregoing the weights of typical unit doses of conventional analgesics and of metoclopramide generally differ in about two orders of magnitude.

In the co-formation of such mixtures of medicaments in tablets it is generally desirable to achieve as uniform as possible a dispersion of the minor medicament by weight, and it is generally necessary to adopt some form of "wet" formulation technique, in order to ensure this, for example wet granulation.

Surprisingly, we have found that the tablets of the present invention, having a good uniform dispersion of the metoclopramide or its salt throughout the tablet may be obtained by direct compression of a powder mixture of the ingredients.

The tablets also give relief of gastro-intestinal symptoms associated with migraine.

The following Examples illustrate the present invention:

TABLE

| Ingredients | Weights, mg | |
|---|---|---|
| | Formulation A | Formulation B |
| Paracetamol D.C. (96% pure) | 520 | 520 |
| Metoclopramide hydrochloride monohydrate | 5.25 | 5.25 |
| Avicel PH102 | 125 | — |
| Maize Starch | — | 43 |
| Sta-Rx 1500 (modified starch) | — | 43 |
| Magnesium Stearate | 1.3 | — |
| Stearic Acid | — | 4.0 |
| Aerosil 200 (colloidal silica) | 0.7 | 0.7 |

EXAMPLE 1

Tablets of Formulation A in the above Table were prepared as follows:

The Avicel PH102 (30 mesh), the metoclopramide salt (60 mesh) and a quarter of the paracetamol D.C. (30 mesh) were mixed for 10 minutes in a planetary mixer. A mixture of the aerosil and an equal volume of the paracetamol (both 30 mesh) together with the remainder of the paracetamol were added to the mixture and mixing continued for a further 30 minutes, followed by addition of the magnesium stearate and a further 5 minutes mixing.

The resultant mixture was compressed on a rotary tabletting machine using ½ in diameter punches.

EXAMPLE 2

The process of Example 1 was repeated for formulation B in the above Table replacing:

Avicel PH102 by maize starch and Sta-Rx 1500 and magnesium stearate by stearic acid.

What we claim is:

1. An analgesic tablet, which comprises an effective amount of paracetamol in combination with metoclopramide or an acid addition salt thereof, the weight ratio of paracetamol to metoclopramide or acid addition salt thereof being from 80:1 to 120:1, respectively.

2. A tablet according to claim 1, wherein the paracetamol in paracetamol D.C.

3. A tablet according to claim 1, wherein the metoclopramide or its acid addition salt is present in an amount of from 0.25 to 2.0 percent by weight.

4. A tablet according to claim 1, which contains from 0.4 to 0.6 g of paracetamol and from 4 to 6 mg of metoclopramide or an acid addition salt thereof.

5. A method of treating migraine headache, which comprises administering to the sufferer an effective amount of a mixture of paracetamol in combination with metoclopramide or an acid addition salt thereof in the form of one or more tablets according to claim 1.

* * * * *